(12) United States Patent
Aoki et al.

(10) Patent No.: US 8,454,820 B2
(45) Date of Patent: Jun. 4, 2013

(54) ELECTROCHEMICAL MOLECULAR RECOGNITION PROBES

(75) Inventors: Hiroshi Aoki, Tsukuba (JP); Hiroaki Tao, Tsukuba (JP); Akiko Kitajima, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 294 days.

(21) Appl. No.: 12/872,735

(22) Filed: Aug. 31, 2010

(65) Prior Publication Data

US 2011/0056844 A1 Mar. 10, 2011

(30) Foreign Application Priority Data

Sep. 9, 2009 (JP) .................. 2009-208400
Oct. 22, 2009 (JP) .................. 2009-242921

(51) Int. Cl.
*G01N 27/327* (2006.01)
(52) U.S. Cl.
USPC ........ 205/792; 204/400; 204/403.01; 435/6.1
(58) Field of Classification Search
USPC ................ 204/400, 403.01; 205/792; 436/6.1
See application file for complete search history.

(56) References Cited

U.S. PATENT DOCUMENTS 7,169,614 B2 1/2007 Umezawa et al.
2005/0153285 A1 7/2005 Umezawa et al.

FOREIGN PATENT DOCUMENTS

| JP | 3956214 B2 | 5/2007 |
| JP | 2010-008253 | * 1/2010 |
| WO | WO 95/13399 A1 | 5/1995 |
| WO | WO 2009/157219 | * 12/2009 |

OTHER PUBLICATIONS

Sato et al, Journal of Organometallic Chemistry 689, 2004, pp. 4722-4728.*
Watanabe et al, Analytical Chemistry 83, 2010, pp. 7290-7296.*
Sanjay Tyagi, et al., Molecular Beacons: Probes that Fluoresce upon Hybridization, Nature Biotechnology vol. 14, Mar. 1996, pp. 303-308.
Chunhai Fan, et al., Electrochemical interrogation of conformational changes as a reagentless method for the sequence-specific detection of DNA, Institute for Polymers and Organic Solids, PNAS, Aug. 5, 2003, vol. 100, No. 16, pp. 9134 to 9137.
Yoshio Umezawa, et al., Ion Channel Sensors Based on Artificial Receptors, Analytical Chemistry, Sep. 1, 2004, vol. 76, No. 17, pp. 321 to 326.

(Continued)

*Primary Examiner* — Kaj K Olsen
(74) *Attorney, Agent, or Firm* — Knobbe, Martens, Olson & Bear LLP

(57) ABSTRACT

Constitute a molecular recognition probe comprising: an electrochemically active group; an activity suppression group that suppresses an electrochemical activity of the electrochemically active group; a receptor area where a molecule of a target substance is specifically recognized; and a molecule area where a steric structure is changed as a result of molecular recognition; wherein the electrochemically active group is suppressed of its activity by the activity suppression group before the molecule is recognized and restores its activity after the molecule is recognized; or constitute a molecular recognition sensor by providing an anchor area on the molecular recognition probe and fixing it on a surface of an electrode.

17 Claims, 5 Drawing Sheets

OTHER PUBLICATIONS

Yi Xiao, et al., Label-Free Electronic Detection of Thrombin in Blood Serum by Using an Aptamer-Based Sensor., Angew. Chem. Int. Ed. 2005, vol. 44, pp. 5456 to 5459.

Brian R. Baker, et al., An Electronic, Aptamer-Based Small-Molecule Sensor for the Rapid, Label-Free Detection of Cocaine in Adulterated Samples and Biological Fluids, J. Am. Chem. Soc. 2006, vol. 128, pp. 3138 to 3139, published on web Feb. 18, 2006.

Hiroshi Aoki, et al., Label- and marker-free gene detection based on hybridization-induced conformational flexibility changes in a ferrocene-PNA conjugate probe., The Royal Society of Chemistry 2007, Analyst, 2007, vol. 132, pp. 784 to 791, published on web Jun. 22, 2007.

Yi Xiao, et al., Electrochemical Detection of Parts-Per-Billion Lead via an Electrode-Bound DNAzyme Assembly, J. Am. Chem. Soc. 2007, vol. 129, pp. 262 to 263, published on web Dec. 20, 2006.

Hiroshi Aoki, et al., Gene Detection Method based on Supramolecular Electrochmistry, Tokyo Conference 2009 Proceedings, Sep. 2, 2009, The Japan Society for Analytical Chemistry, p. 312.

Hiroshi Aoki, et al., Label-free and 'signal-on' DNA detection using a probe DNA terminated with ferrocene and B-cyclodextrin, Supramolecular Chemistry, vol. 22, Nos. 7-8, Jul.-Aug. 2010, Jun. 23, 2010, pp. 455 to 460.

* cited by examiner

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial
<220> FEATURE:
<223> OTHER INFORMATION: DNA sequence in molecule 1

<400> SEQUENCE: 1
gcaaccttcc ctattactcc ac                                              22

<210> SEQ ID NO 2
<211> LENGTH: 22
<212> TYPE: DNA
<213> ORGANISM: Artificial
<220> FEATURE:
<223> OTHER INFORMATION: Full matched DNA as target

<400> SEQUENCE: 2
gtggagtaat agggaaggtt gc                                              22

<210> SEQ ID NO 3
<211> LENGTH: 22
<212> TYPE: DNA
<213> ORGANISM: Artificial
<220> FEATURE:
<223> OTHER INFORMATION: Mismatched DNA as control

<400> SEQUENCE: 3
tttttttttt tttttttttt tt                                              22

<210> SEQ ID NO 4
<211> LENGTH: 22
<212> TYPE: DNA
<213> ORGANISM: Artificial
<220> FEATURE:
<223> OTHER INFORMATION: One-base mismatched DNA as control

<400> SEQUENCE: 4
```

-continued

```
gtggagtaat acggaaggtt gc                                    22

<210> SEQ ID NO 5
<211> LENGTH: 22
<212> TYPE: DNA
<213> ORGANISM: Artificial
<220> FEATURE:
<223> OTHER INFORMATION: DNA sequence in molecule 2

<400> SEQUENCE: 5
gcaaccttcc ctattactcc ac                                    22

<210> SEQ ID NO 6
<211> LENGTH: 22
<212> TYPE: DNA
<213> ORGANISM: Artificial
<220> FEATURE:
<223> OTHER INFORMATION: DNA sequence in probe molecule 3

<400> SEQUENCE: 6
gcaaccttcc ctattactcc ac                                    22
```

ELECTROCHEMICAL MOLECULAR RECOGNITION PROBES

CROSS-REFERENCE TO RELATED APPLICATIONS

This application claims benefit of Japanese Patent Application No. 2009-208400, filed Sep. 9, 2009, and Japanese Patent Application No. 2009-242921, filed Oct. 22, 2009, under 35 USC 119(a), the disclosure of which is herein incorporated by reference in its entirety.

SEQUENCE LISTING

Pursuant to 37 CFR 1.52(e), the material in the ASCII text file submitted as Sequence_Listing_KOD272A-001AUS, created on Aug. 12, 2010, with a size of 1,462 bytes, is hereby expressly incorporated by reference in its entirety.

BACKGROUND OF THE INVENTION

1. Field of the Invention

The present invention relates to a molecular recognition probe that expresses electrochemical activity upon recognition of a target molecule, particularly a molecular recognition probe that sequence-specifically expresses electrochemical activity upon recognition of a target nucleic acid, as well as a molecular recognition sensor and electrochemical detection method based on the same.

2. Description of the Related Art

To detect a specific molecule in a solution where multiple molecules coexist, some physical or chemical perturbation is given by using as an indicator a physical/chemical characteristic unique to this molecule, and the obtained signal change is used to identify the molecule.

If the target molecule has no unique characteristic, a molecular group and the like having a characteristic is used to label the molecule and the target molecule is detected by using this label as an indicator. If labeling the target molecule is difficult, in many cases a target recognition reagent that can specifically recognize the target molecule is used, and a characteristic is given to the target recognition reagent to detect the target molecule. Particularly when there are many measuring targets, the latter method is often exploited.

There are growing needs in recent years for high-throughput screening of biomaterials such as nucleic acids, proteins, peptides, and comprehensive bioactivity analyses such as genome analysis, proteome analysis, and metabolome analysis. New detection methods to replace conventional labeling methods are being desired as the scales of measuring targets continue to increase.

Currently when detecting a nucleic acid in genome analysis, for example, the nucleic acid is directly labeled with a fluorescent moiety to be measured (=target nucleic acid) and the target nucleic acid is sequence-specifically hybridized with another nucleic acid having a sequence complementary thereto and immobilized on a chip or substrate (=probe nucleic acid), after which fluorescence is directly detected to identify the target nucleic acid.

If many types of nucleic acids are measured, however, performing this labeling process for all nucleic acids is very cumbersome and label-free nucleic acid detection methods are desired. Such a situation is the same in proteome analysis and metabolome analysis where many proteins and peptides must be handled.

For example, the molecular beacon method is one of the most frequently used methods among label-free nucleic acid detecting methods. As shown in FIG. 6, in this method, both ends of the probe nucleic acid are modified, respectively, with a fluorescent group (F) and a quenching group (Q) that quenches fluorescence from the fluorescent group. When the probe nucleic acid is not hybridized with the target nucleic acid, a hairpin structure is formed where the quenching group is positioned near the fluorescent group to suppress emission of fluorescence. Only when the probe nucleic acid is hybridized with the target nucleic acid, then the fluorescent group is separated from the quenching group and emits fluorescence, thereby indicating the existence of the target nucleic acid (Patent Literature 1, Non-patent Literature 1).

However, while such detection methods based on fluorescence spectroscopy achieve detection with high sensitivity, it also requires a large, expensive measuring equipment consuming a lot of energy.

The inventors for the present invention had been developing simple methods to replace the fluorescence spectroscopy method. In this process, the inventors demonstrated that electrochemical methods would permit simple detection because the detection is possible using a small, inexpensive apparatus consuming less energy. Particularly, needs for simple diagnosis tools are lately increasing further; toxicogenomics, pharmacogenomics, and other technologies, which are diagnosis technologies based on deviations from normalcy in the workings of genes and proteins in a living body and provide patients with pathological prediction and choices for treatment, are seeing an expansion of their application fields from laboratory-level research to clinical diagnosis.

For example, as a label-free electrochemical molecular recognition method, an ion channel sensor was developed by the inventors (Patent Literatures 2, 3, Non-patent Literature 2). This method was developed by focusing on the function of channel protein present in biomembranes to control the flow of a large amount of ions inside and outside of the biomembranes as this protein binds with a small amount of ligand, and specifically this sensor detects the target substance based on molecular recognition and consequent signal amplification. A molecule that can selectively bind to the target substance is fixed on the electrode surface as a receptor and an electrochemically active species (marker) is dissolved in the measurement solution. As the target substance binds to the receptor and condenses at the electrode surface, electron transfer reaction of the marker is facilitated or suppressed at the electrode surface. By putting in place such mechanism, presence of a small amount of the target substance can be detected as a flow of a large mount of electrons. The biggest advantage of this principle is that the target substance can be detected electrochemically even when the target substance itself has no electrochemical activity (=even though the target substance is not labeled). The inventors successfully detected, with high sensitivity, many different molecules, ions, sugar chains, peptides and nucleic acids.

The inventors then advanced this principle one step further and developed a receptor having electrochemical activity, consequently proposing an even simpler method that not only eliminates the need to label the target substance, but also eliminates the need to add a marker (Non-patent Literature 3). Take a receptor for nucleic acid detection (probe nucleic acid), for example. One end of this probe nucleic acid is modified with ferrocene or other electrochemically active group, while the other end is fixed to the electrode surface. It is known that nucleic acids have a very flexible structure in single-stranded form, but assume a rigid structure in double-stranded form. Paying attention to this nature of nucleic acids, the inventors found that sequence-specific detection of the target nucleic acid is possible from a decrease in the observed current, because ferrocene at the end of the probe nucleic acid changes its state, upon hybridization, from one where electron transfer reaction occurs freely at the electrode surface, to one where such reaction is difficult. Detection of various target substances such as proteins, molecules, ions and other types of chemical species using similar methods has also been attempted (Non-patent Literatures 4 to 7).

However, such detection method using a receptor with an electrochemically active species appended at its end must depend on control of electron transfer reaction whose principle is in turn dependent on the distance from the electrode surface, and therefore the mechanism becomes such that a molecular recognition event is notified by a decrease in electron transfer reaction. Almost all probe nucleic acids based on an electrochemical detection principle adopt such mechanism. In general, a system whose signal decreases upon molecular recognition ("signal-off" type) is associated with low detection sensitivity. In contrast, a system whose signal increases upon molecular recognition ("signal-on" type) can expect high detection sensitivity. To develop an analysis method that provides the simplicity of an electrochemical method while eliminating the needs for both labeling and marker, it is necessary to develop a "signal-on" type method. However, no such method has been developed to date.

PRIOR ART LITERATURES

Patent Literatures

[Patent Literature 1] International Patent Publication No. WO95/13399
[Patent Literature 2] Japanese Patent No. 3,956,214
[Patent Literature 3] U.S. Pat. No. 7,169,614

Non-Patent Literatures

[Non-patent Literature 1] Nature Biotechnol. vol. 14, 303-308 (1996)
[Non-patent Literature 2] Anal. Chem. vol. 76, No. 17, 320A-326A (2004)
[Non-patent Literature 3] Analyst vol. 132, 784-791 (2007)
[Non-patent Literature 4] Angew, Chem. Int. Ed. vol. 44, 5456-5459 (2005)
[Non-patent Literature 5] Proc. Natl. Acad. Sci. USA vol. 100, 9134-9137 (2003)
[Non-patent Literature 6] J. Am. Chem. Soc. vol. 128, 3138-3139 (2006)
[Non-patent Literature 7] J. Am. Chem. Soc. vol. 129, 262-263 (2007)

SUMMARY OF THE INVENTION

The present invention was developed in light of the aforementioned situation, and the object of the present invention is to provide a molecular recognition probe and a molecular recognition sensor which would embody a "signal-on" type detection method where the electrochemical signal increases upon detection of the target substance, without a need for labeling the target substance or adding a marker to the measurement solution.

After repeated studies in earnest to achieve the aforementioned object, the inventors realized an electrochemically active group; an activity suppression group that suppresses an electrochemical activity of the electrochemically active group; a receptor where a molecule of a target substance is specifically recognized; and a molecular recognition probe which has a molecule area where its steric structure is changed as a result of molecular recognition.

The inventors gained the knowledge that the aforementioned object could be achieved by constituting a molecular recognition probe; wherein the electrochemically active group is suppressed of its activity by the activity suppression group before the molecule is recognized and restores its activity after the molecule is recognized; or by constituting a molecular recognition sensor by providing an anchor area on the molecular recognition probe and fixing it on a surface of an electrode.

The present invention was completed based on the aforementioned knowledge and is explained below.

[1] A molecular recognition probe characterized by comprising: an electrochemically active group; an activity suppression group that suppresses an electrochemical activity of the electrochemically active group; a receptor area where a molecule of a target substance is specifically recognized; and a structural change area where a steric structure is changed as a result of molecular recognition; wherein the electrochemically active group is suppressed of its activity by the activity suppression group before the molecule is recognized and restores its activity after the molecule is recognized.

[2] A molecular recognition probe according to [1] above, characterized in that the receptor area serves also as the structural change area.

[3] A molecular recognition probe according to [1] above, characterized by having an anchor area for fixing on a surface of solids.

[4] A molecular recognition probe according to [1] or [2] above, characterized in that the electrochemically active group is constituted by metallocene or any derivative thereof.

[5] A molecular recognition probe according to [1] above, characterized in that the activity suppression group structurally includes the electrochemically active group.

[6] A molecular recognition probe according to [5] above, characterized in that the activity suppression group is constituted by cyclodextrin or calixarene or any derivative thereof.

[7] A molecular recognition probe according to [1] above, characterized in that the electrochemically active group is constituted by metallocene or derivative thereof and the activity suppression group is constituted by cyclodextrin or calixarene or any derivative thereof.

[8] A molecular recognition probe according to [7] above, characterized in that the receptor area serves also as the structural change area.

[9] A molecular recognition probe according to [8] above, characterized by having an anchor area for fixing on a surface of solids.

[10] A molecular recognition sensor fabricated by fixing on a surface of solids a molecular recognition probe according to [3] above.

[11] A molecular recognition sensor fabricated by fixing on a surface of solids a molecular recognition probe according to [9] above.

[12] An electrochemical detection method characterized by detecting a change in electrochemical signal before and after molecular recognition, which signal is produced from the molecular recognition probe upon contacting a solution containing a target substance with the molecular recognition probe of according to [1] above.

[13] An electrochemical detection method according to [12] above, characterized in that the change of electrochemical signal is an increase and decrease of a current value or potential value.

[14] An electrochemical detection method characterized by detecting a change in electrochemical signal before and after molecular recognition, which signal is produced from the molecular recognition probe upon contacting a solution containing a target substance with the molecular recognition probe according to [7] above.

[15] An electrochemical detection method characterized by detecting a change in electrochemical signal before and after molecular recognition, which signal is produced from the molecular recognition probe upon contacting a solution containing a target substance with the molecular recognition probe according to [8] above.

[16] An electrochemical detection method characterized by detecting a change in electrochemical signal before and after molecular recognition, which signal is produced from the molecular recognition sensor upon contacting a solution containing a target substance with the molecular recognition sensor according to [10] above.

[17] An electrochemical detection method characterized by detecting a change in electrochemical signal before and after molecular recognition, which signal is produced from the molecular recognition sensor upon contacting a solution containing a target substance with the molecular recognition sensor according to [11] above.

EFFECTS OF THE INVENTION

The present invention has the characteristics explained above and therefore it can embody a "signal-on" type detection method where the electrochemical signal increases upon recognition of the target substance, without having to label the target substance or adding a marker to the measurement solution.

BRIEF DESCRIPTION OF THE DRAWINGS

These and other features of this invention will now be described with reference to the drawings of preferred embodiments which are intended to illustrate and not to limit the invention. The drawings are oversimplified for illustrative purposes and are not necessarily to scale.

DETAILED DESCRIPTION

The present invention achieved the object of providing a molecular recognition probe and a molecular recognition sensor which would embody a "signal-on" type detection method where the electrochemical signal increases upon detection of the target substance, without a need for labeling the target substance or adding a marker to the measurement solution, by constituting a molecular recognition probe comprising: an electrochemically active group; an activity suppression group that suppresses an electrochemical activity of the electrochemically active group; a receptor where a molecule of a target substance is specifically recognized; and a molecule area where a steric structure is changed as a result of molecular recognition; wherein the electrochemically active group is suppressed of its activity by the activity suppression group before the molecule is recognized and restores its activity after the molecule is recognized.

A molecular recognition probe in the present invention, a receptor that specifically recognizes the molecule of the target substance, can serves also as an area which changes the steric structure by molecular recognition.

In other words, the molecular recognition probe proposed by the present invention is specifically a molecule comprising a receptor that selectively recognizes a target substance by molecular recognition, and a structure change area where its steric structure changes upon molecular recognition, wherein both ends of this have, respectively, an electrochemically active group and an activity suppression group that suppresses the activity of this electrochemically active group; or it is a molecule comprising a receptor that recognizes a target substance by molecular recognition and is capable of changing its steric structure upon molecular recognition, both ends of which receptor have, respectively, an electrochemically active group and an activity suppression group that suppresses the activity of this electrochemically active group.

In addition, the molecular recognition sensor proposed by the present invention is a sensor constituted by fixing this molecular recognition probe on the surface of an electrode.

Figure 1:
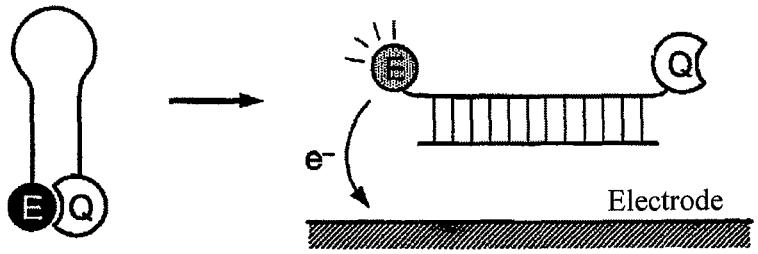
FIG. 1 illustrates a schematic drawing of a molecular recognition probe conforming to the present invention.
Figure 2:
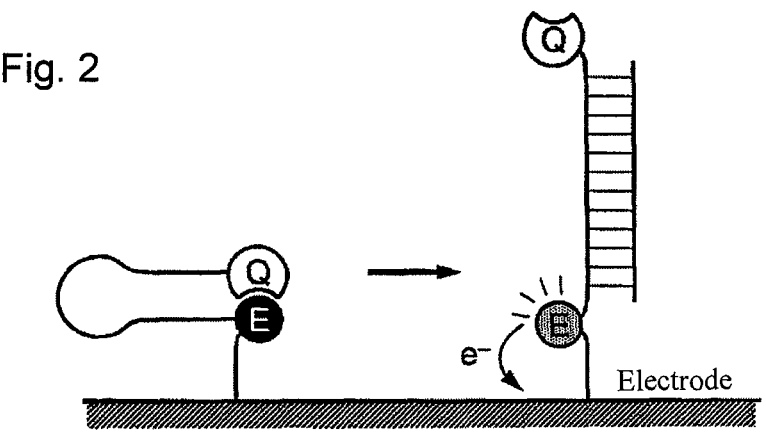
FIG. 2 illustrates a schematic drawing of a molecular recognition sensor conforming to the present invention, where a molecular recognition probe conforming to the present invention is fixed on an electrode.

FIG. 1 is a schematic drawing of a molecular recognition probe conforming to the present invention, while FIG. 2 is a schematic drawing of a molecular recognition sensor having the aforementioned molecular recognition probe fixed on an electrode by providing an anchor area on the molecular recognition probe for fixing it on a surface of solids.

In the figures, E indicates an electrochemically active group, while Q indicates an activity suppression group that suppresses the electrochemical activity of the electrochemically active group. In these figures, a nucleic acid is used as an example of a receptor present between E and Q. The nucleic acid used as a receptor also serves as a molecular area which changes the steric structure by molecular recognition in this example.

As shown in FIGS. 1 and 2, the molecular recognition probe proposed by the present invention and having the aforementioned structure cannot obtain any electrochemical signal before it recognizes the molecule of the target substance because the electrochemically active group is positioned in close proximity with the activity suppression group and therefore the activity of the electrochemically active group is suppressed. Once the molecule of the target substance is recognized, however, the receptor changes its steric structure due to molecular recognition and accordingly the electrochemically active group separates from the activity suppression group and restores its activity, and consequently the molecular recognition probe obtains electrochemical signals.

At this time, the molecular recognition probe generates electrochemical signals in the bulk measurement solution, while the molecular recognition sensor generates electrochemical signals at the electrode surface. In both cases, eventually an electrode is used to measure these electrochemical signals.

Figure 6:
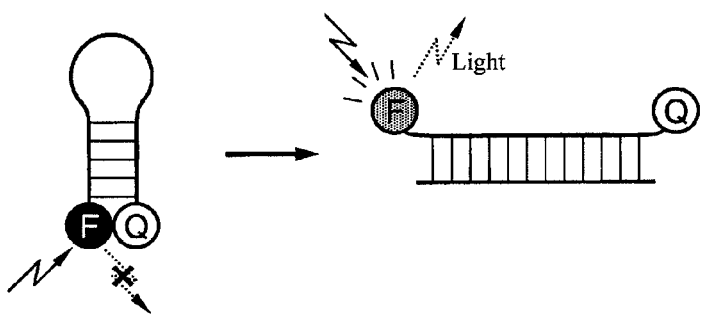
FIG. 6 illustrates a schematic drawing of a conventional molecular beacon method.

The molecular recognition probe desirably has the electrochemically active group and activity suppression group immobilized together with relative weak force by forming an inclusion complex, charge transfer complex, or the like, before the molecule is recognized, in order to remain in close proximity with each other. For the same purpose, it is also possible to form a stem structure like the one shown in FIG. 6 if a nucleic acid is used for the receptor area, for example.

Under the present invention, change in the electrochemical activity of the electrochemically active group may be in the form of an increase or decrease in current or increase or decrease in voltage.

Figure 3:
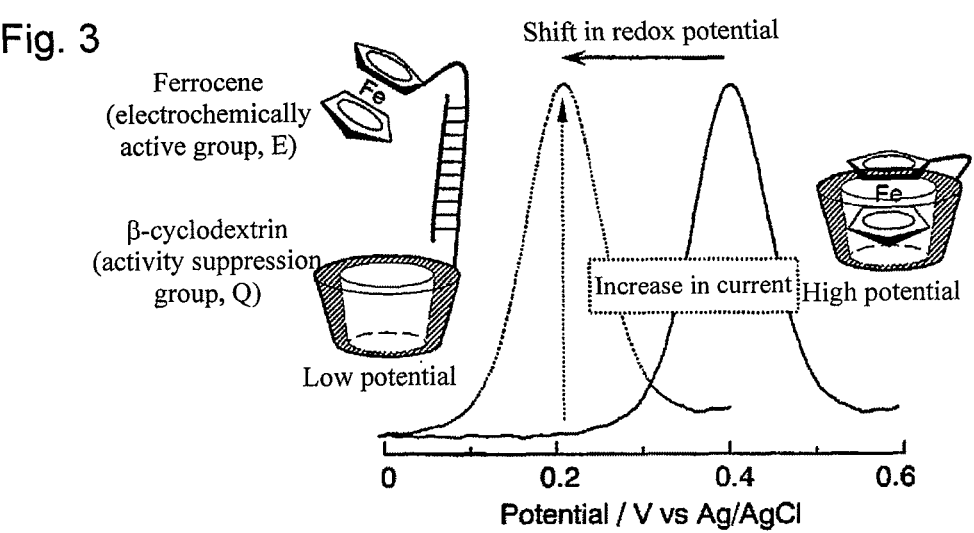
FIG. 3 illustrates a schematic drawing showing that as the receptor recognizes the molecule, its steric structure changes and the redox potential shifts, and consequently the current increases.

FIG. 3 is a schematic drawing showing that as the receptor recognizes the molecule, its steric structure changes and the redox potential shifts, and consequently the current increases.

As explained above, the present invention can embody a "signal-on" type detection method where the electrochemical signal increases upon recognition of the target substance, without having to label the target substance or adding a marker to the measurement solution.

Under the present invention, the aforementioned receptor area may be constituted by a nucleic acid, protein, peptide, ionophore, or the like.

Also under the present invention, the aforementioned structural change area may be constituted by a nucleic acid, protein, peptide, ionophore, or the like.

Specific examples of nucleic acids that can be used for these areas include DNA, RNA, PNA (peptide nucleic acid) and LNA (locked nucleic acid).

The aforementioned receptor area may serve also as the aforementioned structural change area.

Under the present invention, the aforementioned electrochemically active group is ideally a quinone or derivative thereof, naphtoquinone or derivative thereof, anthraquinone or derivative thereof, pyridine or derivative thereof, bipyridine or derivative thereof, thiazine or derivative thereof, metallocene such as ferrocene or derivative thereof or other organic metal complex or redox enzyme.

Under the present invention, the activity suppression group is capable of suppressing the electrochemical activity of the electrochemically active group.

For example, as the activity suppression group, a material including the electrochemically active group is used. In this case, its activity is suppressed because the electrochemically active group is included in the activity suppression group before molecular recognition, whereas, upon molecular recognition, the receptor area changes its steric structure as the molecular recognition progresses, and as a result thereof, it changes to the structure where the electrochemically active group is not included in the activity suppression group, thereby restoring its activity. Examples of such activity suppression groups include cyclodextrin, calixarene and derivatives thereof.

If the electrochemically active group is a redox enzyme, moreover, the activity suppression group may be an inhibitor of such enzyme, in this case, before molecular recognition, the enzymatic activity of redox enzyme is suppressed; however, upon molecular recognition, the receptor area changes its steric structure as the molecular recognition progresses, wherein the enzyme no longer undergoes influence by the inhibitor, thereby restoring the enzymatic activity. Examples of such activity suppression groups include imidazol, triazol and derivatives thereof.

In the present invention, the aforementioned receptor and/or the structure change area may be bound with the aforementioned electrochemically active group and/or the activity suppression group via linker areas.

In this case, the electrochemically active group and/or the activity suppression group can be positioned away from the molecular recognition receptor and/or the structure change area. As a result, the electrochemically active group and/or the activity suppression group do not easily undergo steric hindrance from the receptor and/or the structure change area, whereby the probe in the present invention can be constituted by sufficiently utilizing the effects of the electrochemically active group and/or the activity suppression group.

The linker area may have a structure which has preferably a linear alkylene group (may be substituted) having five or more carbons, and which further has one or more repeating structures of glycol group, ether group, thioether group, amide group, imide group, maleimide group, ester group, or phosphate ester. It may also have any given ring structure or have atom(s) other than carbon, such as sulfur, nitrogen, oxygen, etc., and further it may have a single-bond, double-bond, or triple-bond.

In the present invention, a molecular recognition sensor constituted by the aforementioned molecular recognition probe affixed on an electrode can be fabricated by providing an anchor area through which the molecular recognition probe can be fixed on the surface of solids.

This anchor area is made of a material that can form a covalent bond with the metal being one material constituting the electrode, where specific examples include thiols, thioethers, thioesters, lipoic acid derivatives, cysteine derivatives and other sulfur compounds, among others.

The aforementioned anchor area may also be made of a material that can form a covalent bond with the metal oxide being the other material constituting the electrode, where specific examples include silanes.

Furthermore, the anchor area is ideally fixable on the surface of solids by means of antigen-antibody reaction, His-Tag, nucleic acid hybridization, biotin-avidin bond or formation of other bonds.

Figure 4:
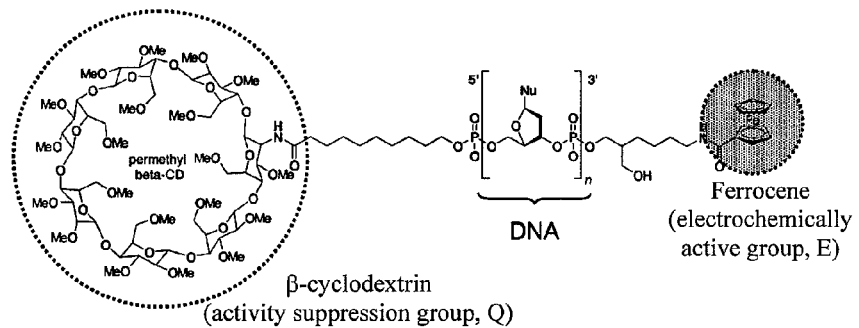
FIG. 4 illustrates a schematic drawing of an example of a molecular recognition probe conforming to the present invention.

FIG. 4 is a schematic drawing of an example of a molecular recognition probe conforming to the present invention, where the electrochemically active group, receptor and activity suppression group are constituted by ferrocene, peptide nucleic acid and β-cyclodextrin, respectively. In the example shown in FIG. 4, as a linker for ferrocene and nucleic acid, and a linker for nucleic acid and β-cyclodextrin, a phosphate ester structure having a linear alkylene group is used respectively.

Figure 5:
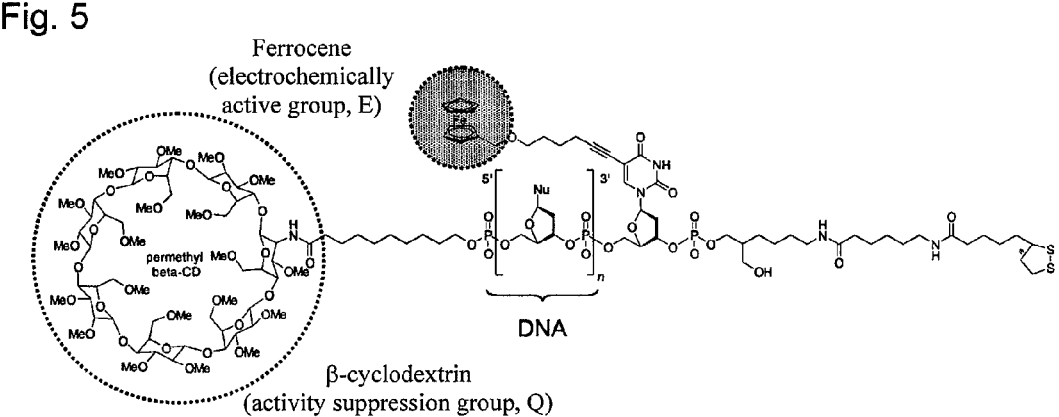
FIG. 5 illustrates a drawing showing an example of an anchor added to the molecular recognition probe illustrated in FIG. 4.

FIG. 5 shows an example of an anchor added to this probe.

To electrochemically detect a target substance in a solution by using the molecular recognition probe or molecular recognition sensor according to the present invention, the solution containing the target substance and the molecular recognition probe or molecular recognition sensor are placed in contact with each other, and then a change of electrochemical signal before and after molecular recognition, whose change is produced from the molecular recognition probe or molecular recognition sensor, is detected.

In the present invention, a method of contacting a solution containing a target substance and the molecular recognition probe or molecular recognition sensor is not limited to, but includes, for example, a method in which the molecular recognition probe of the present invention is used, where an electrode is inserted into a container containing a solution comprising a target substance and the molecular recognition probe, or a method where droplets of a solution comprising a target substance to which the molecular recognition probe is mixed are dropped on a substrate on which electrodes are formed. Also, when the molecular recognition sensor of the present invention is used, a method can be used where the sensor is inserted into a container containing a solution comprising a target substance, or where droplets of a solution comprising a target substance are dropped on a substrate having the sensor.

EXAMPLES

The following explains synthesizing molecular recognition probes conforming to the present invention, as well as DNA detection using synthesized probes, by using examples. It should be noted that the present invention is not limited to these examples.

<Preparation>

(1) Reagent

Figure 7:
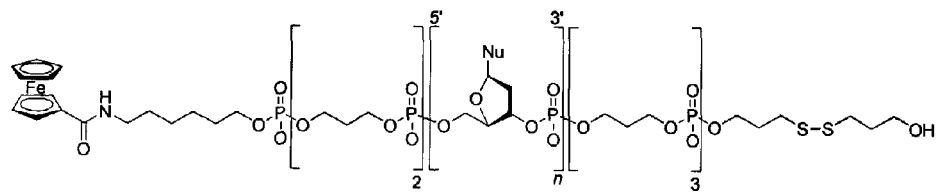
FIG. 7a illustrates a drawing showing the structural formula of molecule 1.
FIG. 7b illustrates a drawing showing the structural formula of molecule 2.
FIG. 7c illustrates a drawing showing the structural formula of molecule 3.
Figure 7:
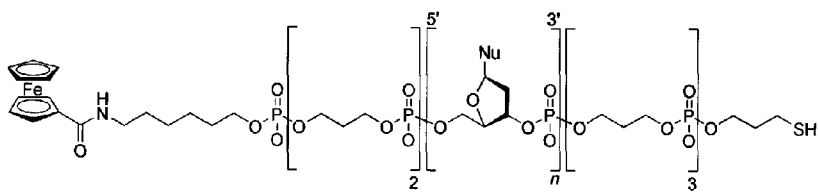
Figure 7:
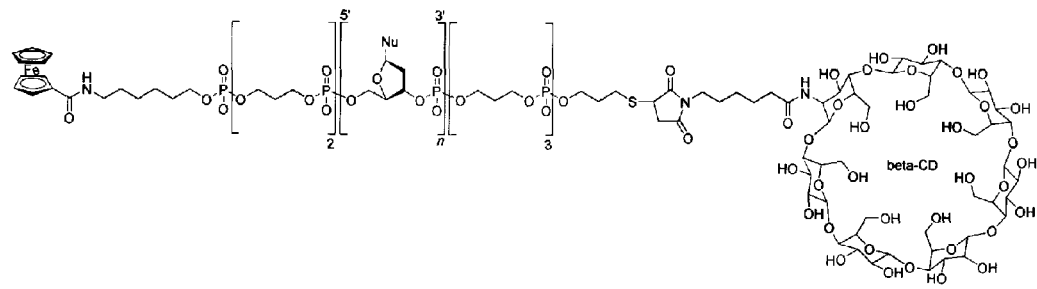

A dithioled DNA modified with ferrocene (molecule 1), produced by a DNA synthesizer, was purchased from Fasmac. The structural formula of molecule 1 is Fc-C6-(C3)$_2$-GCA ACC TTC CCT ATT ACT CCA C—(C3)$_3$—(CH$_2$)$_3$—SS—(CH$_2$)$_3$OH (where Fc is ferrocene, and C6 and C3 are linkers having a carbon length of 6 and 3, respectively) (5'-end and 3'-end modified product of sequence in SEQ ID No: 1). FIG. 7a shows the structural formula of this molecule. Changing the dithiol group of this molecule to the thiol group made it possible to immobilize β-cyclodextrin to this molecule. As the targets for the probe, a fully matched DNA (sequence: 5'-GTG GAG TAA TAG GGA AGG TTG C-3') (SEQ ID No: 2), mismatched DNA (sequence: (dT)$_{22}$) (SEQ ID No: 3) and one-base mismatched DNA (sequence: 5'-GTG GAG TAA TAC GGA AGG TTG C-3') (SEQ ID No: 4) were purchased from Operon Biotechnologies, where all targets were prepared into a 100 μM aqueous solution and stocked. 3A-amino-3A-deoxy-(2AS, 3AS)-β-cyclodextrin was purchased from Tokyo Chemical Industry, while N-(6-maleimidocaproyloxy) sulphosuccinimide sulfuric acid salt was purchased from Dojindo Laboratories (Kumamoto). All other chemicals used were of availably highest grade. All aqueous solutions were prepared with ultrapure water (specific resistance>18.2 MΩcm) obtained with a Milli-Q water system (Millipore, Bedford, Mass.).

(2) Electrochemical measurement

Carbon-based interdigitated array electrodes (width 10 μm, gap 5 μm, length 2 mm, number of pairs 65, BAS, Tokyo) were used. Reference electrodes were formed by applying Ag/AgCl chloride paste followed by heating for 5 minutes at 120° C. All electrochemical measurements were performed at 25° C. using an ALS-730C electrochemical measuring equipment (BAS). Cyclic voltammograms were measured with the four-electrode configuration in the dual model. The potential was scanned from 0 V to 0.6 V, and then back to 0 V, at a scan rate of 10 mV/s.

Example 1

Synthesis of the Probe

50 μL of 1 OD molecule 1 aqueous solution and 5 μL of 0.1 M sodium phosphate buffer solution (pH 7.0) containing 1 M dithiothreitol were mixed together and placed for 1 hour at 37° C. Thereafter, 150 μL of water was added, and the mixture was added to a NAP-5 column (GE Healthcare Life Science, Tokyo) equilibrated in advance with water, and fractioned in units of 500 μL by using water as the eluent. The obtained fractions were measured using an absorption spectrometer and the fraction having the highest absorbance at 260 nm was used in the subsequent synthesis. The structural formula of the obtained molecule was Fc-C6-(C3)$_2$-GCA ACC TTC CCT ATT ACT CCA C—(C3)$_3$—(CH$_2$)$_3$—SH (molecule 2) (5'-end and 3'-end modified product of sequence in SEQ ID No: 5), and the concentration of this molecule was calculated by using molar absorption coefficient ε=2.29×10$^{-5}$ M$^{-1}$ cm$^{-1}$ to be 7.51 μM (500 μL). FIG. 7b shows the structural formula of this molecule.

500 μL of 0.1 M sodium phosphate buffer solution (pH 7.0) containing 5 mM 3A-amino-3A-deoxy-(2AS, 3AS)-β-cyclodextrin, 0.1 M sodium chloride and 1 mM ethylene diamine tetraacetate and 125 μL of 0.1 M sodium phosphate buffer solution (pH 7.0) containing 4 mM N -(6-maleimidocaproyloxy) sulfosuccinimide sulfuric acid salt, 0.1 M sodium chloride and 1 mM ethylene diamine tetraacetate were mixed together and stirred for 1 hour at 30° C. To this solution, molecule 2 was added at a mol ratio of 1:10 and the resulting mixture was placed for 20 hours at 4° C. Thereafter, the mixture was freeze-dried and condensed into a liquid volume of 200 μL, and the condensed mixture was added to a NAP-5 column equilibrated in advance with water, and fractioned in units of 500 μL by using water as the eluent. The obtained fractions were measured using an absorption spectrometer and the fraction having the highest absorbance at 260 nm was used as the target compound (molecule 3, probe). The structural formula of the probe was Fc-C6-(C3)$_2$-GCA ACC TTC CCT ATT ACT CCA C—(C3)$_3$—(CH$_2$)$_3$—S-Mal-β-CD (where Mal indicates a maleimide cross-linker) (5'-end and 3'-end modified product of sequence in SEQ ID No: 6). It was prepared into a 100 μM aqueous solution and stocked. FIG. 7c shows the structural formula of this molecule.

Example 2

Figure 8:
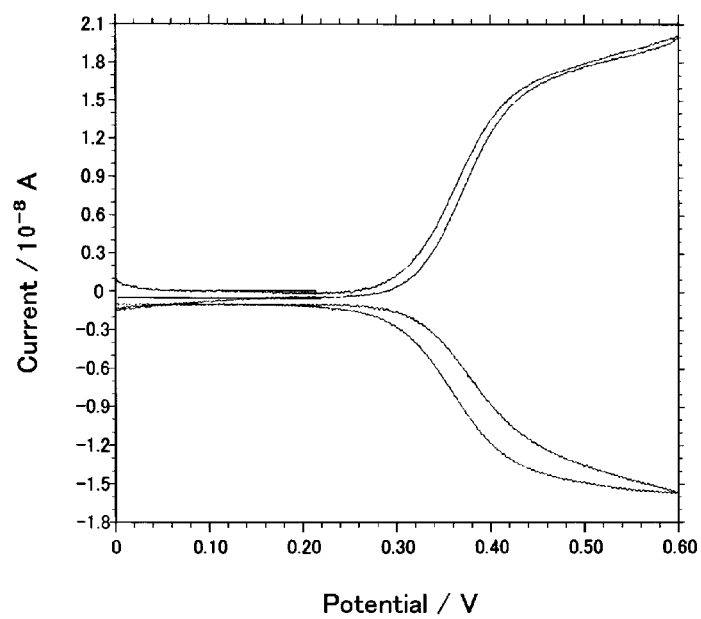
FIG. 8a illustrates a graph showing a sigmoidal current-potential curve (after subtracting a background current-potential curve) exhibited by a solution containing a synthesized probe.
FIG. 8b illustrates a graph showing the results of differentiating the sigmoidal current-potential curve exhibited by a solution containing a synthesized probe.
Figure 8:
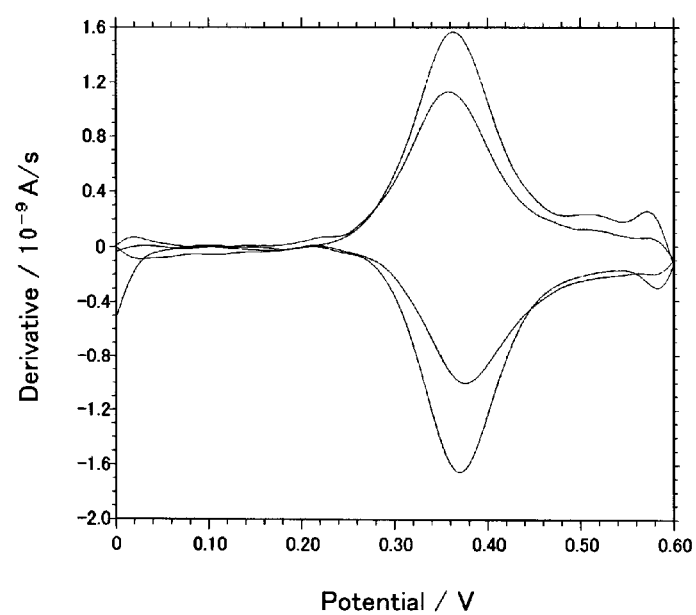

Electrochemical Detection of DNA Using the Probe 0.1 M phosphate buffer solution (pH 7.0) containing 0.01 M sodium chloride was mixed together with 100 μM probe aqueous solution at a ratio of 3:1 v/v, to prepare a 75 mM phosphate buffer solution containing 25 μM probe and 7.5 mM sodium chloride. Using carbon-based interdigitated array electrodes, electrochemical measurement of 5 μL of this solution was performed at a scan rate of 10 mV/s between 0 and 0.6 V (relative to the Ag/AgCl electrode), and a sigmoidal current-potential curve was obtained due to the electron transfer reaction of ferrocene modified to the probe. From this curve, a current-potential curve of 75 mM phosphate buffer solution containing 7.5 mM sodium chloride was subtracted as the background. Although the current was around 0 between 0 and 0.3 V, a rapid increase in current was observed from near 0.3 V, and at around 0.4 V the current became roughly constant at 18 nA (FIG. 8a). The potential at the inflection point in this curve was 0.363 V induced from the differentiation of the curve (FIG. 8b). Subsequently, change in the current-potential curve was evaluated by the potential at the inflection point.

Figure 9:
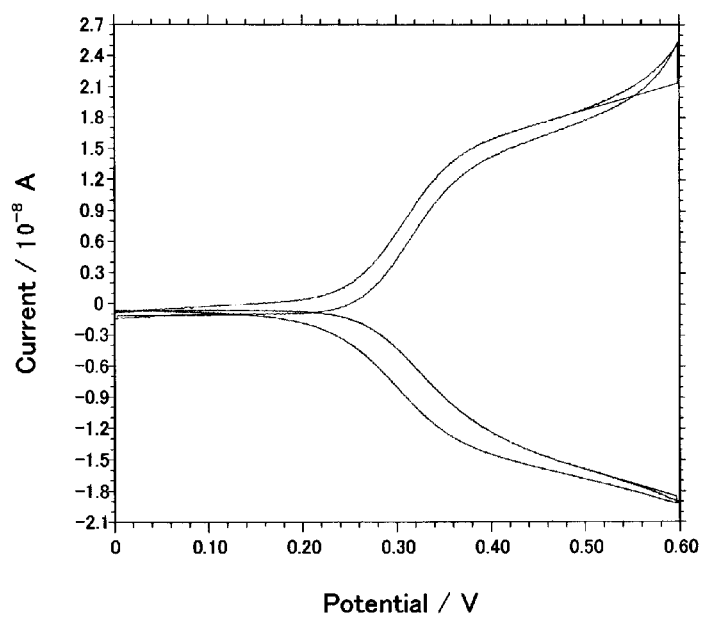
FIG. 9a illustrates a graph showing a sigmoidal current-potential curve (after subtracting a background current-potential curve) exhibited by a solution containing a synthesized probe and a fully matching DNA.
FIG. 9b illustrates a graph showing the results of differentiating the sigmoidal current-potential curve exhibited by a solution containing a synthesized probe and a fully matching DNA.
Figure 9:
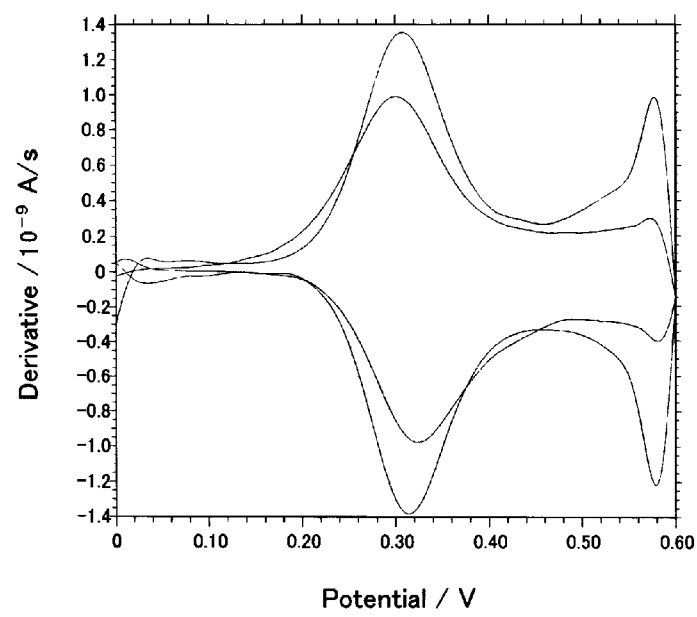

0.2 M phosphate buffer solution (pH 7.0) containing 0.02 M sodium chloride, 100 µM probe, 100 µM fully matched DNA and water were mixed together at a ratio of 3:2:2:1 v/v, to prepare a 75 mM phosphate buffer solution containing 25 µM probe, 25 µM fully matched DNA and 7.5 mM sodium chloride. When carbon-based interdigitated array electrodes were used to perform electrochemical measurement of 5 µL of this solution, a sigmoidal current-potential curve was obtained (FIG. 9a). The background was subtracted and the potential at the inflection point in this curve was induced from differentiation to be 0.301 V (FIG. 9b). Compared to the use of the probe alone, the potential was negatively shifted by 62 mV. This negative potential shift was due to the hybridization of the probe with the fully matched DNA that caused ferrocene, immobilized to the probe, to undergo electron transfer reaction more easily. This shows that DNA can be detected using the electrochemical detection method based on this probe, by using a shift in redox potential as an indicator.

Similarly when we focused on the change in current at a potential of 0.3 V in the sigmoidal current-potential curve (FIG. 9a) shown in the previous item, the current increased from 1 nA to 7 nA before and after the hybridization. This was because the hybridization of the probe with the fully matched DNA caused ferrocene, immobilized to the probe, to undergo electron transfer reaction more easily. This shows that DNA can be detected using the electrochemical detection method based on this probe, by using an increase in redox current as an indicator. The result also shows that electrochemical detection of "signal-on" type, where the signal increases upon molecular detection, was also possible.

In the present disclosure where conditions and/or structures are not specified, the skilled artisan in the art can readily provide such conditions and/or structures, in view of the present disclosure, as a matter of routine experimentation. Further, in the present disclosure, the term "the present invention" is intended to refer to some embodiments of the present invention.

It will be understood by those of skill in the art that numerous and various modifications can be made without departing from the spirit of the present invention. Therefore, it should be clearly understood that the forms of the present invention are illustrative only and are not intended to limit the scope of the present invention.

We claim:

1. A molecular recognition probe characterized by comprising: an electrochemically active group; an activity suppression group that suppresses an electrochemical activity of the electrochemically active group; a receptor area where a molecule of a target substance is specifically recognized; and a structural change area where a steric structure is changed as a result of molecular recognition; wherein the electrochemically active group is suppressed of its activity by the activity suppression group before the molecule is recognized and restores its activity after the molecule is recognized.

2. A molecular recognition probe according to claim 1, characterized in that the receptor area serves also as the structural change area.

3. A molecular recognition probe according to claim 1, characterized by having an anchor area for being fixed on a surface of solids.

4. A molecular recognition sensor fabricated by fixing on a surface of solids a molecular recognition probe according to claim 3.

5. An electrochemical detection method characterized by detecting a change in electrochemical signal before and after molecular recognition, which signal is produced from the molecular recognition sensor upon contacting a solution containing a target substance with the molecular recognition sensor according to claim 4.

6. A molecular recognition probe according to claim 1, characterized in that the electrochemically active group is constituted by metallocene or any derivative thereof 7. A molecular recognition probe according to claim 1, characterized in that the activity suppression group forms an inclusion complex with the electrochemically active group.

8. A molecular recognition probe according to claim 7, characterized in that the activity suppression group is constituted by cyclodextrin or calixarene or any derivative thereof.

9. A molecular recognition probe according to claim 1, characterized in that the electrochemically active group is constituted by metallocene or derivative thereof and the activity suppression group is constituted by cyclodextrin or calixarene or any derivative thereof.

10. A molecular recognition probe according to claim 9, characterized in that the receptor area serves also as the structural change area.

11. A molecular recognition probe according to claim 10, characterized by having an anchor area for being fixed on a surface of solids.

12. A molecular recognition sensor fabricated by fixing on a surface of solids a molecular recognition probe according to claim 11.

13. An electrochemical detection method characterized by detecting a change in electrochemical signal before and after molecular recognition, which signal is produced from the molecular recognition sensor upon contacting a solution containing a target substance with the molecular recognition sensor according to claim 12.

14. An electrochemical detection method characterized by detecting a change in electrochemical signal before and after molecular recognition, which signal is produced from the molecular recognition probe upon contacting a solution containing a target substance with the molecular recognition probe according to claim 10.

15. An electrochemical detection method characterized by detecting a change in electrochemical signal before and after molecular recognition, which signal is produced from the molecular recognition probe upon contacting a solution containing a target substance with the molecular recognition probe according to claim 9.

16. An electrochemical detection method characterized by detecting a change in electrochemical signal before and after molecular recognition, which signal is produced from the molecular recognition probe upon contacting a solution containing a target substance with the molecular recognition probe of according to claim 1.

17. An electrochemical detection method according to claim 16, characterized in that the change of electrochemical signal is an increase and decrease of a current value or potential value.

* * * * *

UNITED STATES PATENT AND TRADEMARK OFFICE
CERTIFICATE OF CORRECTION

PATENT NO. : 8,454,820 B2
APPLICATION NO. : 12/872735
DATED : June 4, 2013
INVENTOR(S) : Aoki et al.

Page 1 of 1

It is certified that error appears in the above-identified patent and that said Letters Patent is hereby corrected as shown below:

On title page 2, column 2, item [56] at line 5, Under Other Publications, delete "Electrochmistry," and insert --Electrochemistry,--.

In the Specification
Column 2 at line 47, delete "mount" and insert --amount--.

In the Claims
Column 13 at line 53, Claim 6, delete "thereof" and insert --thereof.--.

Signed and Sealed this
Second Day of September, 2014

Michelle K. Lee
*Deputy Director of the United States Patent and Trademark Office*